United States Patent [19]

Héja et al.

[11] Patent Number: 4,709,081

[45] Date of Patent: Nov. 24, 1987

[54] PROCESS FOR THE PREPARATION OF DIPHENYL ETHER DERIVATIVES

[75] Inventors: Gergely Héja; Dezsó Korbonits; Endre Pálosi; Pál Kiss; Csaba Gönczi; Ida Szvoboda née Kanzel; Ede Márványos; Judit Kun; Mária Szomor née Wundele; Gábor Szabó; Tamás Kállay; László Ledniczky, all of Budapest, Hungary

[73] Assignee: Chinoin Gyogyszer es Vegyeszeti Termekek Gyara R.T., Budapest, Hungary

[21] Appl. No.: 781,303

[22] Filed: Sep. 26, 1985

Related U.S. Application Data

[63] Continuation of Ser. No. 281,478, Jul. 8, 1981, abandoned.

[30] Foreign Application Priority Data

Jul. 10, 1980 [HU] Hungary .............................. 1719/80

[51] Int. Cl.[4] .............................................. C07C 69/76
[52] U.S. Cl. ................................. 560/100; 560/105; 560/107; 560/121; 560/123; 560/124; 560/254; 560/255; 560/55; 568/636; 260/410.5
[58] Field of Search ................ 560/100, 55, 105, 107, 560/121, 123, 124, 125, 255; 568/636; 260/410.5

[56] References Cited

U.S. PATENT DOCUMENTS 3,985,779  10/1976  Tanaka ................................ 560/100

FOREIGN PATENT DOCUMENTS 6144373  8/1973  Japan .
0302379  1/1979  Japan .
1579151  11/1980  United Kingdom .

OTHER PUBLICATIONS

Bonner & Castro, *Essentials of Modern Organic Chemistry*, p. 265, 1965.
Chem. Ber. 63,1930, pp.: 855-869—"Gunther Lock: Zur Kenntnis der . . . " (1930).

*Primary Examiner*—Paul J. Killos
*Attorney, Agent, or Firm*—Karl F. Ross; Herbert Dubno; Jonathan Myers

[57] ABSTRACT

The invention relates to a process for the preparation of compounds of formula (I)

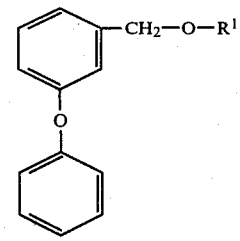

wherein
$R^1$ stands for hydrogen or the group $COR^2$, wherein
$R^2$ stands for a straight or branched chained alkyl having 1 to 8 carbon atoms optionally substituted with phenyl, naphthyl, tetrahydronaphthyl or m-phenoxy-benzyl, cycloalkyl having 3 to 6 carbon atoms optionally substituted with one or more straight or branched chained alkyl or alkenyl having 1 to 6 carbon atoms, phenyl or naphthyl.

The compounds of formula (I) are prepared according to the invention by
(a) reacting esters of formula (II)

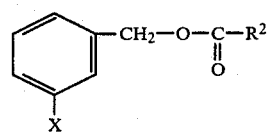

wherein
X stands for chlorine or bromine and
$R^2$ has the same meanings as defined above with a phenol alkali metal salt and
(b) if desired converting the diphenyl ethers so obtained to a specific compound of formula (I), m-phenoxybenzyl alcohol by the hydrolysis of the ester group.

11 Claims, No Drawings

PROCESS FOR THE PREPARATION OF DIPHENYL ETHER DERIVATIVES

This is a continuation of co-pending application Ser. No. 281,478 filed on 8 July 1981.

This invention relates to a process for the preparation of compounds of formula (I)

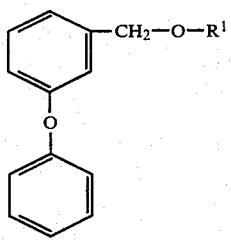

wherein
$R^1$ is hydrogen or $COR^2$, wherein
$R^2$ is a straight or branched chained alkyl having 1 to 8 carbon atoms and which can be substituted with phenyl, naphthyl, tetrahydronaphthyl or m-phenoxy-benzyl, cycloalkyl having 3 to 6 carbon atoms which can be substituted with one or more straight or branched chained alkyl or alkenyl having 1 to 6 carbon atoms, phenyl or naphthyl.

It is known that compounds of formula (I) are important intermediates in the preparation of pharmaceuticals and plant protecting agents or are effective insecticides for the plant protection. In consequence of their great industrial importance many processes for the synthesis of these compounds are known.

A specific compound of formula (I), the m-phenoxybenzyl alcohol (in formula (I) $R^1$ is hydrogen) is prepared from 3-hydroxytoluene in many ways. The common feature of these syntheses are that 3-hydroxytoluene (m-cresol) is first converted to 3-phenoxytoluene then the m-phenoxybenzyl alcohol is prepared by the oxidation conversion of the methyl group followed by a reduction step. The oxidation of 3-phenoxytoluene is also performed by the partial halogenation of the methyl group followed by hydrolysis and reduction (U.S. Pat. No. 4,065,505, Hungarian Pat. No. 170,866, German Auslegeschrift Nos. 2,605,678; 2,757,031; 2,604,473; 2,604,474; 2,651,371; 2,402,457; 2,471,764; 2,744,603; 2,707,603, 2,707,232; 2,704,512; and Belgian Pat. No. 809,867).

According to the Japanese Kokaku No. 61443/73 ether-formation is performed by the reaction of m-hydroxybenzyl acetate and benzyl halides in the presence of a copper catalyst and the acetate of m-phenoxybenzyl alcohol is obtained. In this process the yield is, however, moderate and the synthesis route is long.

Compounds of formula (I), wherein $R^1$ is $COR^2$, are prepared by the esterification of m-phenoxybenzyl alcohol obtained from m-cresol and the corresponding acid component in a known manner. This method is described in many articles, monographs and patent applications (e.g. Chem. Soc. Revs. 7, 473 (1978), Aldrichimica Acta Vol. 9 No. 3, 49 (1976)).

Some compounds of formula (I) are prepared by the reaction of m-phenoxybenzyl halides obtained from m-phenoxytoluene and metal salts of carboxylic acids as well. So reaction mixtures containing many components are obtained from which a uniform product can be produced only by combination of several chemical procedures (German Auslegeschrift No. 2,707,232; Belgian Pat. No. 809,867).

All the above mentioned processes have the disadvantages that the starting materials (pure m-cresol free from isomers, m-hydroxybenzyl alcohol) are hardly available, the oxidation of m-phenoxytoluene does not result in a uniform product (this is also the situation in the halogenation reaction) and the separation of the reaction mixture is complicated.

It is known that the m-bromobenzyl alcohol, which can be prepared from benzaldehyde of low cost and ready availability, decomposes under alkaline conditions (Chem. Ber. 63, 855 (1930)), so it cannot be the starting material of the Ullmann reaction (ether formation).

This disadvantage can be eliminated according to Japanese Kokaku No. 03023/79, representing the newest state of the art. According to this patent application the less labile m-chlorobenzyl alcohol is used as starting material and is etherified with an alkali metal salt of phenol to m-phenoxybenzyl alcohol in the presence of a copper salt catalyst. During the long reaction time (heating for 24 hours) the starting material also sustains an injury or undesirable side reactions proceed and the yield calculated on the m-phenoxybenzyl alcohol is moderate (38%).

In contradiction to the above it has now been surprisingly found that compounds of formula (I), wherein $R^1$ stands for the group $COR^2$, can be prepared in a simply and industrially readily accomplishable manner in high yields by the reaction of a compound of formula (II)

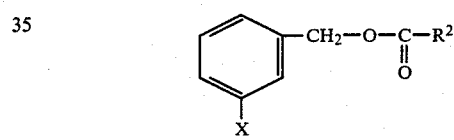

wherein
X stands for chlorine or bromine and
$R^2$ has the same meanings as defined above, with an alkali metal salt of phenol and if desired by the hydrolysis of the ester group when a specific compound of formula (I), the m-phenoxy benzyl alcohol is formed.

According to our invention the ether-formation is performed by heating the ester of formula (II) with an alkali phenolate in an anhydrous solvent medium or in a melt in the presence of a metal catalyst. At the alkali phenolate, preferably potassium phenolate is used in a 10 to 50 mole% excess. As solvents nonpolar organic solvents—preferably xylene—or polar solvents—preferably pyridine or phenol—or the mixture thereof can be used. If the reaction is carried out in a melt a diluent, preferably phenol is used.

As catalysts copper and/or copper(I) salts—preferably copper(I) chloride—are employed in an amount of 0.05 to 0.3 mol%.

The ether formation is carried out at a temperature of from 130° C. to 210° C., preferably between 140° C. and 180° C.

The 3-phenoxybenzyl alcohol esters obtained during the ether-formation can be converted to 3-phenoxybenzyl alcohol in a known manner by acid or alkaline hydrolysis, preferably in an aqueous organic solvent, particularly an aqueous methanol medium. The hydrolysis can be carried out also preferably with an ion exchange resin catalyst. As acid catalysts, mineral acids, preferably hydrochloric acid, sulfuric acid or an acid ion exchange resin are preferred. As alkaline catalysts alkali metal hydroxides, preferably sodium hydroxide or potassium hydroxide can be used.

The starting materials of formula (II) are prepared by the halogenation of benzaldehyde, the reduction of the m-halogen-benzaldehyde obtained and the acylation of the m-halogenbenzyl alcohol so obtained with an acid anhydride or acid halide. In this manner the esters of formula (II) can be prepared in high yields.

It has been surprisingly found that the looseness of the aromatic halogen group in m-halogenbenzyl alcohols acylated with carboxylic acids is increased in comparison to the m-halogenbenzyl alcohols significantly which results, apart from an increase in the yield, in the reducibility of the reaction time.

So while m-phenoxybenzyl alcohol can be obtained by heating m-bromobenzyl acetate with potassium phenolate in xylene in the presence of small amounts of pyridine and copper(I) chloride for three hours to the boiling point in 77% yield, using m-bromobenzyl alcohol under similar reaction conditions the desired m-phenoxybenzyl alcohol can be obtained, however, only in traces.

The m-chlorobenzyl alcohol can be etherified with a potassium phenolate melt containing phenol at a temperature of 160° C. for five hours in 73% yield. According to example 2 of the Japanese Kokaku No. 03023/79 the m-chlorobenzyl alcohol can be etherified at a temperature of 176° to 178° C. by heating for 24 hours and the yield is only 38%.

Further details of the process of the invention are shown in the following examples.

EXAMPLE 1

10.35 g. (0.11 mole) of phenol, 6.15 g. (0.11 mole) of potassium hydroxide and 35 cm³. of xylene are weighed together. The water is azeotropically distilled with stirring and boiling. 5 cm³. of pyridine and 0.5 g. of copper(I) chloride are added then 22.91 g. (0.1 mole) of 3-bromobenzyl acetate are dropped into the reaction mixture during 15 minutes with stirring and boiling. The reaction mixture is boiled with stirring for an additional three hours. After cooling the reaction mixture is filtered off and the filtrate washed with a mixture of 25 cm³. of 15% sodium chloride solution and 2 cm³. of 40% sodium hydroxide solution. The organic phase is evaporated in vacuo. The residue is distilled in vacuo and so 18.65 g. of 3-phenoxybenzyl acetate are obtained. Boiling point 142°–145° C./53.2 Pa, $n_D^{20}$: 1.5621, yield 77%.

EXAMPLE 2

28.29 g. (0.3 mole) of phenol, 11.2 g. (0.2 mole) of potassium hydroxide and 20 cm³. of xylene are weighed together. The water is azeotropically distilled with stirring and boiling then the xylene is also distilled. To the reaction mixture 1.0 g. of copper(I) chloride and 1.0 g. of activated copper are added and in oil bath of 180° C. 22.91 g. (0.1 mole) 3-bromobenzyl acetate are dropped during 25 minutes while stirring. The reaction mixture is stirred at the same temperature for an additional two hours. After cooling 50 cm³. of 15% sodium chloride solution are added to the reaction mixture, then the reaction mixture is filtered off. The filtrate is extracted twice with 30 cm³ of toluene. The united organic phase is washed with a mixture of 30 cm³. of 15% sodium chloride solution and 10 cm³. of 40% sodium hydroxide solution. The organic phase is evaporated and the residue distilled in vacuo. 17.2 g. of 3-phenoxybenzyl acetate are obtained. Boiling point 142°–145° C./53.2 Pa, $n_D^{20}$: 1.5621, yield 71%.

EXAMPLE 3

18.07 g. (0.192 mole) of phenol, 8.42 g. (0.15 mole) of potassium hydroxide and 20 cm³ of xylene are weighed together. The water is azeotropically distilled with stirring and boiling then the xylene is also distilled. To the reaction mixture 1.0 g. of copper(I) chloride and 1.0 g. of activated copper are added and in oil bath of 160° C. 18.07 g. (0.1 mole) of 3-chlorobenzyl acetate are dropped during 70 minutes then stirred at the same temperature for four hours. After cooling 25 cm³. of toluene are added to the reaction mixture, then the reaction mixture is filtered off and washed with 25 cm³. of toluene. The filtrate is washed with a mixture of 30 cm³. 15% sodium chloride solution and 2 cm³. 40% sodium hydroxide solution. The organic phase is evaporated and the residue is distilled in vacuo. 17.68 g. of 3-phenoxybenzyl acetate are obtained. Boiling point 138°–144° C./40 Pa, $n_D^{20}$: 1.562, yield 73%.

EXAMPLE 4

2.42 g. (0.01 mole) of 3-phenoxybenzyl acetate, 5 cm³. of methanol and 5 cm³. of 2N sodium hydroxide solution are refluxed for three hours. Then the methanol is distilled off and the organic phase is dissolved in 30 cm³. of methylene chloride, washed with 10 cm³. of 1N hydrochloric acid solution and 10 cm³. of water. 1.90 g. of 3-phenoxybenzyl alcohol are obtained. $n_D^{20}$: 1.593, yield 95%.

EXAMPLE 5

2.42 g. (0.01 mole) of 3-phenoxybenzyl acetate, 5 cm³. of methanol and 5 cm³. of 2N hydrochloric acid solution are refluxed for three hours. Then the methanol is distilled off. The organic phase is dissolved in 30 cm³. of methylene chloride, washed with 10 cm³. of water, 10 cm³. of 1N sodium hydroxide solution and 10 cm³. of water then evaporated. 1.8 g. of 3-phenoxybenzyl alcohol are obtained. $n_D^{20}$: 1.593, yield 90%.

EXAMPLE 6

2.42 g. (0.01 mole) of 3-phenoxybenzyl acetate, 10 cm³. of methanol, 10 cm³. of water and 0.2 g. of acid ion exchange resin (Nafion H) are refluxed with stirring for nine hours. After cooling the reaction mixture is filtered off and evaporated. The residue is dissolved in 30 cm³. of methylene chloride, washed with 10 cm³. of 1N sodium hydroxide solution and 10 cm³. of water then evaporated. 1.8 g. of 3-phenoxybenzyl alcohol are obtained. $n_D^{20}$: 1.593, yield 90%.

EXAMPLE 7

Into a solution of 55.7 g. (0.298 mole) of 3-bromobenzyl alcohol in 50 cm³. of benzene 36.5 g. (0.357 mole) of acetic acid anhydride are dropped during 30 minutes while boiling. The reaction mixture is refluxed for an additional six hours. After cooling the reaction mixture is diluted with 100 cm³ of benzene and washed with 100 cm³. of water thoroughly. The organic phase is separated, evaporated and the residue distilled in vacuo. 62.8 g. of 3-bromo benzyl acetate are obtained. Boiling point 100°–104° C./53.2 Pa, $n_D^{20}$: 1.5435, yield 92%.

EXAMPLE 8

Into a solution of 84.4 g. (0.592 mole) of 3-chlorobenzyl alcohol in 40 cm$^3$. of benzene 61.5 g. (0.6 mole) of acetic acid anhydride are dropped during 15 minutes while boiling. The reaction mixture is refluxed with 100 cm$^3$. of benzene and washed with 100 cm$^3$. of water thoroughly. The organic phase is separated and evaporated. 105.2 g. of 3-chlorobenzyl acetate are obtained which is suitable to ether-formation. $n_D^{20}$: 1.5226, yield 96%.

EXAMPLE 9

Analogous as in example 1 using, however, 28.5 g. of m-bromobenzyl diethyl acetate instead of m-bromobenzyl acetate 23.8 g. 3-phenoxybenzyl diethyl acetate are obtained. Boiling point 160° C./26 Pa, yield 80%.

EXAMPLE 10

Analogous as in example 4 using, however, 2.98 g. of 3-phenoxybenzyl diethyl acetate instead of 3-phenoxybenzyl acetate 1,92 g. of 3-phenoxybenzyl alcohol are obtained. $n_D^{20}$: 1.5935, yield 95%.

EXAMPLE 11

Into a solution of 321 g. of 3-bromo benzaldehyde, 220 cm$^3$ of 30% formaldehyde and 600 cm$^3$. of methanol one-third of the solution of 300 g. of potassium hydroxide in 300 cm$^3$. of water are dropped at 50° C. while stirring then the reaction mixture is stirred at this temperature for 1 hour. The temperature is raised to 60° C. and at this temperature the second third part of the base solution are dropped into the reaction mixture. After stirring the reaction mixture 1 hour at 60° C. the temperature is rised to 70° C. and at this temperature the last part of the base solution is dropped into the reaction mixture. The reaction mixture is stirred 1 hour at 70° C. then cooled to ambient temperature. The pH-value of the reaction mixture is adjusted with concentrated hydrochloric acid solution between 7.5 to 8 while maintaining the temperature at 40° C. From this reaction mixture 500 cm$^3$. of methanol is distilled off, 500 cm$^3$. of water are added to the residue then extracted twice with 150 cm$^3$ of 1,2-dichloro ethane. From the united organic phase the water is removed by azeotropic distillation then 200 cm$^3$. of acetic acid anhydride are dropped into the dichloro ethane solution while boiling and stirring. After boiling for 6 hours the reaction mixture is cooled, washed with 500 cm$^3$. of water and 500 cm$^3$. of 10% sodium hydrogen carbonate solution then evaporated. The residue is distilled in vacuo. 287.2 g. of 3-bromobenzyl acetate are obtained. Boiling point 123°–125° C./1200 Pa, $n_D^{24}$: 1.5406, yield 72%.

EXAMPLE 12

71 g. of 3-chlorobenzyl alcohol, 60 cm$^3$. of acetic acid and 1 g of p-toluene sulfonic acid are refluxed for 5 hours then the excess of acetic acid distilled off in vacuo. The residue is dissolved in 100 cm$^3$. of 1,2-dichloro ethane and the solution washed with 10% sodium hydrogen carbonate solutin then with water and evaporated. The residue is distilled in vacuo. 85.5 g. of 3-chlorobenzyl acetate are obtained. Boiling point 105°–110° C./933.4 Pa, $n_D^{25}$: 1.5185, yield 93%.

EXAMPLE 13

Analogous to example 12 using, however, 93.5 g. of 3-bromobenzyl alcohol instead of 3-chlorobenzyl alcohol 105,3 g. of 3-bromobenzyl acetate are obtained. Boiling point 100°–104° C., $n_D^{20}$: 1.5430, yield 92%.

EXAMPLE 14

Into a solution of 370 g. of 3-bromo benzaldehyde, 900 cm$^3$. of methanol and 300 g. of 40% formaldehyde the solution of 380 g. of potassium hydroxide in 300 cm$^3$. of water are dropped at a temperature of from 48° to 52° C. during 10 minutes while stirring. The reaction mixture is stirred for 3.5 hours at a temperature of from 50° to 55° C. Into this reaction mixture the solution of 60 g. of potassium hydroxide in 40 cm$^3$. of water are dropped at 55° C. then the reaction mixture is stirred at 60° C. for 1.5 hours. After cooling to ambient temperature the pH-value of the reaction mixture is adjusted with 250 cm$^3$. of an aqueous hydrochloric acid solution /1:1/ to 9. From this reaction mixture the methanol is distilled off, 2 l. of water are added to the residue and twice extracted with 400 cm$^3$. of 1,2-dichloro ethane. After distilling the dichloro ethane off the residue is fractionated in vacuo. 333 g. of 3-bromobenzyl alcohol are obtained. Boiling point 120°–122° C./266–399 Pa.

EXAMPLE 15

A solution of 136 g. of diethyl acetic acid, 147.5 g. of 3-chlorobenzyl alcohol and 1 g. of p-toluene sulfonic acid in 300 cm$^3$. of toluene is boiled until finishing the water formation. After cooling the solution is washed with a solution containing 15% of sodium chloride and 10% of sodium carbonate then evaporated. 249 g. of 3-chlorobenzyl diethyl acetate are obtained which can be used directly in example 16.

EXAMPLE 16

Analogous as in example 3 using, however, 24 g. of 3-chlorobenzyl diethyl acetate instead of 3-chlorobenzyl acetate 20.8 g. of 3-phenoxybenzyl diethyl acetate are obtained. Boiling point 160° C./26 Pa.

EXAMPLE 17

Analogous as in example 15 using, however, 192.6 g. of 3-bromobenzyl alcohol instead of 3-chlorobenzyl alcohol 293 g. 3-bromobenzyl diethyl acetate are obtained which can be used directly in example 9.

We claim:

1. A process for the preparation of a compound of the formula (I)

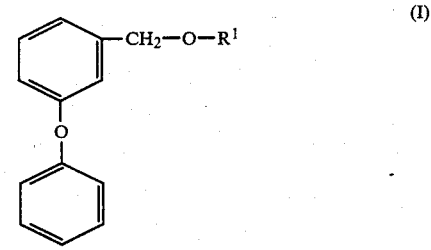

wherein

R$^1$ is hydrogen or COR$^2$, and R$^2$ is a straight or branched chain alkyl having 1 to 8 carbon atoms which can be substituted with phenyl, naphthyl, tetrahydronaphthyl, or m-phenoxy-benzyl; cycloalkyl having 3 to 6 carbon atoms which can be substituted with one or more straight or branched alkyl or alkenyl groups having 1 to 6 carbon atoms, phenyl or naphthyl, which comprises etherifying an ester of the formula (II)

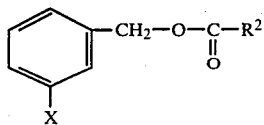
(II)

where X is chlorine or bromine with a phenol alkali metal salt, the latter present in a 10 to 100 mole % excess, to yield a compound of the formula (I) wherein $R^1$ is $COR^2$ and in the case where the compound of the formula (I) to be produced is directed to $R^1$ as hydrogen, hydrolyzing the compound of the formula (I) where $R^1$ is $COR^2$ to yield the desired product.

2. The process defined in claim 1 wherein the diphenyl ether so obtained is converted to m-phenoxybenzyl alcohol by the hydrolysis of the ester group.

3. The process defined in claim 1 which comprises heating the ester of the formula (II) in a solution or a melt with phenol sodium or phenol potassium salt in the presence of copper and/or a copper (I) salt in an anhydrous medium.

4. The process defined in claim 1 which comprises performing the ether formation in a nonpolar or polar organic solvent or in a melt in the presence of phenol as diluent.

5. The process defined in claim 3 which comprises performing the ether formation at a temperature from 190° to 210° C.

6. The process defined in claim 4 which comprises performing the ether formation at a temperature from 190° to 210° C.

7. The process defined in claim 5 wherein said temperature is 140° to 180° C.

8. The process defined in claim 6 wherein said temperature is 140° to 180° C.

9. The process defined in claim 2 which comprises performing the hydrolysis with acid or base catalysts with a mineral acid or with an alkali metal hydroxide or with an acid ion exchange resin.

10. The process defined in claim 9 which comprises performing the hydrolysis in a mixture of water and an organic solvent.

11. The process defined in claim 10 wherein said mixture is aqueous methanol.

* * * * *